US006468238B1

(12) United States Patent
Hawkins et al.

(10) Patent No.: US 6,468,238 B1
(45) Date of Patent: Oct. 22, 2002

(54) HALO CROWN

(75) Inventors: J. Riley Hawkins, Cumberland, RI (US); John Knapik, Jacksonville, FL (US); Eric Smith, Chagrin Falls, OH (US)

(73) Assignee: Depuy Acromed, Inc., Raynham, MA (US)

( * ) Notice: Subject to any disclaimer, the term of this patent is extended or adjusted under 35 U.S.C. 154(b) by 0 days.

(21) Appl. No.: 09/687,135

(22) Filed: Oct. 13, 2000

(51) Int. Cl.[7] .................................................. A61F 5/00
(52) U.S. Cl. .............................. 602/17; 602/36; 606/54
(58) Field of Search .............................. 602/17, 36–37, 602/18–19, 33, 40; 128/DIG. 23; 606/130, 54, 56, 59; A61F 5/00

(56) References Cited

U.S. PATENT DOCUMENTS

| 4,667,660 A | 5/1987 | Eingorn |
| 4,838,264 A | 6/1989 | Kesselman et al. |
| 4,913,135 A | 4/1990 | Mattingly |
| 5,122,132 A | 6/1992 | Bremer |
| 5,156,588 A | 10/1992 | Marcune et al. |
| 5,203,765 A | * 4/1993 | Friddle, Jr. .................. 602/18 |
| 5,456,266 A | 10/1995 | Brown |
| 5,674,186 A | * 10/1997 | Guigui et al. .................. 602/17 |
| 5,697,895 A | * 12/1997 | Bremer ........................ 602/37 |

FOREIGN PATENT DOCUMENTS

WO     WO98/30167     7/1998

OTHER PUBLICATIONS

PCT Search Report for PCT/US 01/32075 dated Feb. 2, 2002.

* cited by examiner

*Primary Examiner*—Danton D. DeMille
*Assistant Examiner*—Quang Thanh D
(74) *Attorney, Agent, or Firm*—Andrew C. Farmer; Theodore Shatynski

(57) ABSTRACT

A halo crown has depending posterior legs adjustable in multiple dimensions for conveniently adjusting the halo crown to a patient's skull. Each leg slides along a single axis yet provides adjustments in three dimensions due to a portion thereof extending downwardly, inwardly and rearwardly and the orientation of the axis.

15 Claims, 4 Drawing Sheets

HALO CROWN

FIELD OF THE INVENTION

This invention relates to a halo crown having positionally adjustably elements capable of being fitted into a plurality of positions in multiple dimensions.

BACKGROUND

Halo crowns are used to stabilize the cervical region of the spine and comprise an arch which encircles at least a portion of the skull and pins for attaching the arch to the skull. Typically, halo crowns are provided in a variety of sizes to accommodate varying skull sizes.

SUMMARY OF THE INVENTION

A medical halo according to the present invention provides enhanced adjustability over prior halos. It comprises an elongated first arch shaped to generally extend about a portion of the periphery of an individual's head and to lie in laterally spaced relation thereto. At least one leg extends posteriorly from the first arch and over a posterior portion of the individual's head. The leg is moveable along a first axis having a posterior-anterior component. At least one contact member is provided on the leg. Preferably, the contact member is a pin clamp.

The leg preferably comprises a first portion extending posteriorly from and slidably attached to the first arch and a second portion depending inferiorly from the first portion. Preferably, the second portion also extends medially and also extends inferiorly with the first axis also having a posterior-inferior component. Preferably, the first axis also has a medial-lateral component.

Preferably, movement of the first portion along the first axis in one direction moves the second portion inferiorly, posteriorly and laterally, and movement of the first portion along the first axis in an opposite direction moves the second portion superiorly, anteriorly and medially.

A positioning pad can be provided on the first arch and preferably is elastomeric and shaped to elastically fit onto the first arch.

A second arch can be provided which is connected to the first arch and out of planar relationship with the first arch to provide rigidity to the first arch.

Preferably, the first arch is injection molded.

Preferably, the first arch comprises at least one channel formed therein with at least a portion of the leg slideably disposed within the channel.

Preferably, the halo has two legs.

Preferably, the halo has at least one slideable member slideably affixed to the first arch and bearing a contact member, such as a pin clamp. The first arch and the slideable member preferably have complimentary interlocking shapes such that the slideable member is slideable along the first arch yet can not rotate around the first arch.

Preferably, the slideable member can be affixed to the first arch after the medical halo has been installed on the individual's head. One way in which this can be accomplished is to provide the slideable member in a first section and a second section which are separable from one another.

DETAILED DESCRIPTION

Figure 1:
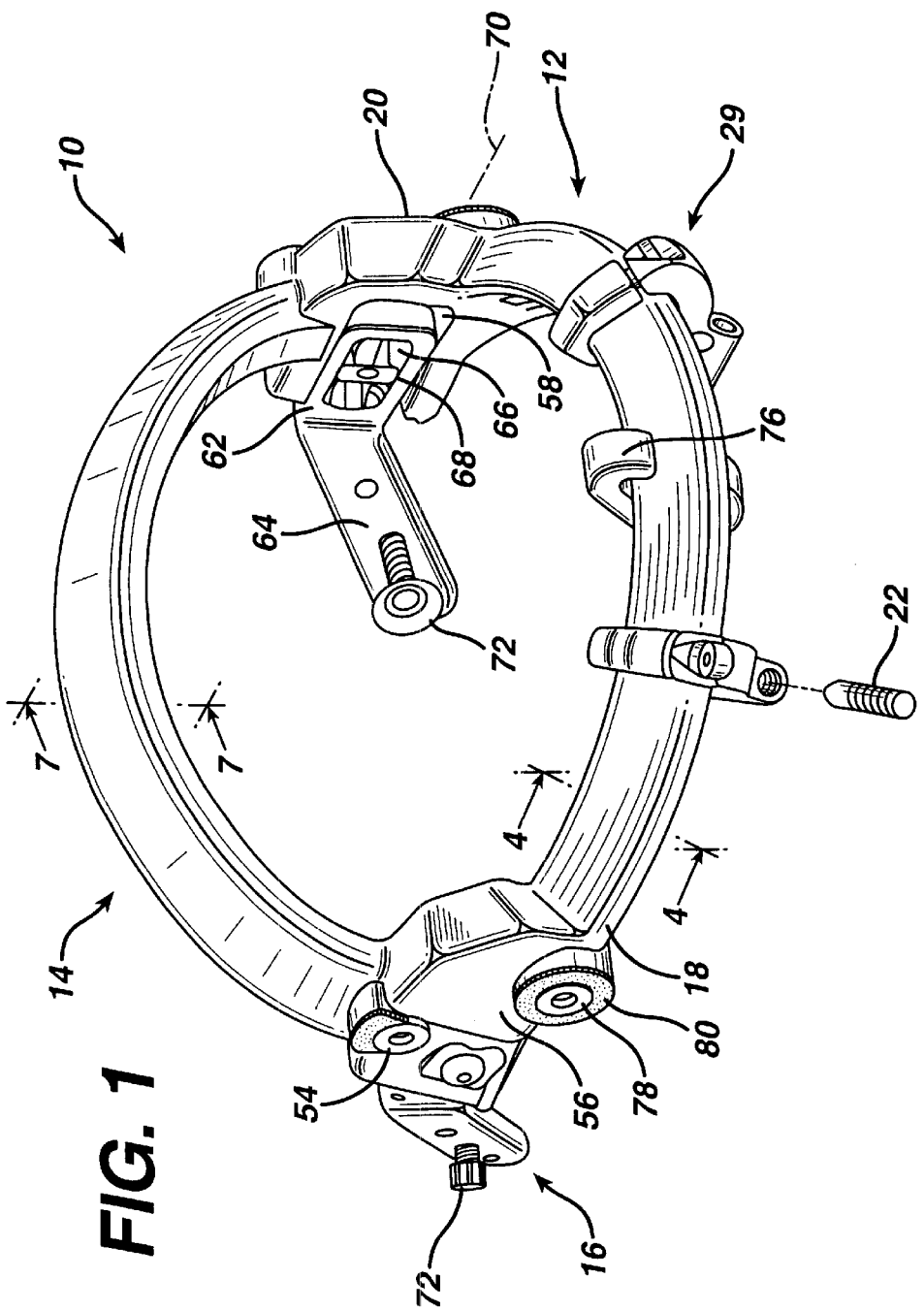
FIG. 1 is a perspective view of a halo crown according to the invention.
Figure 2:
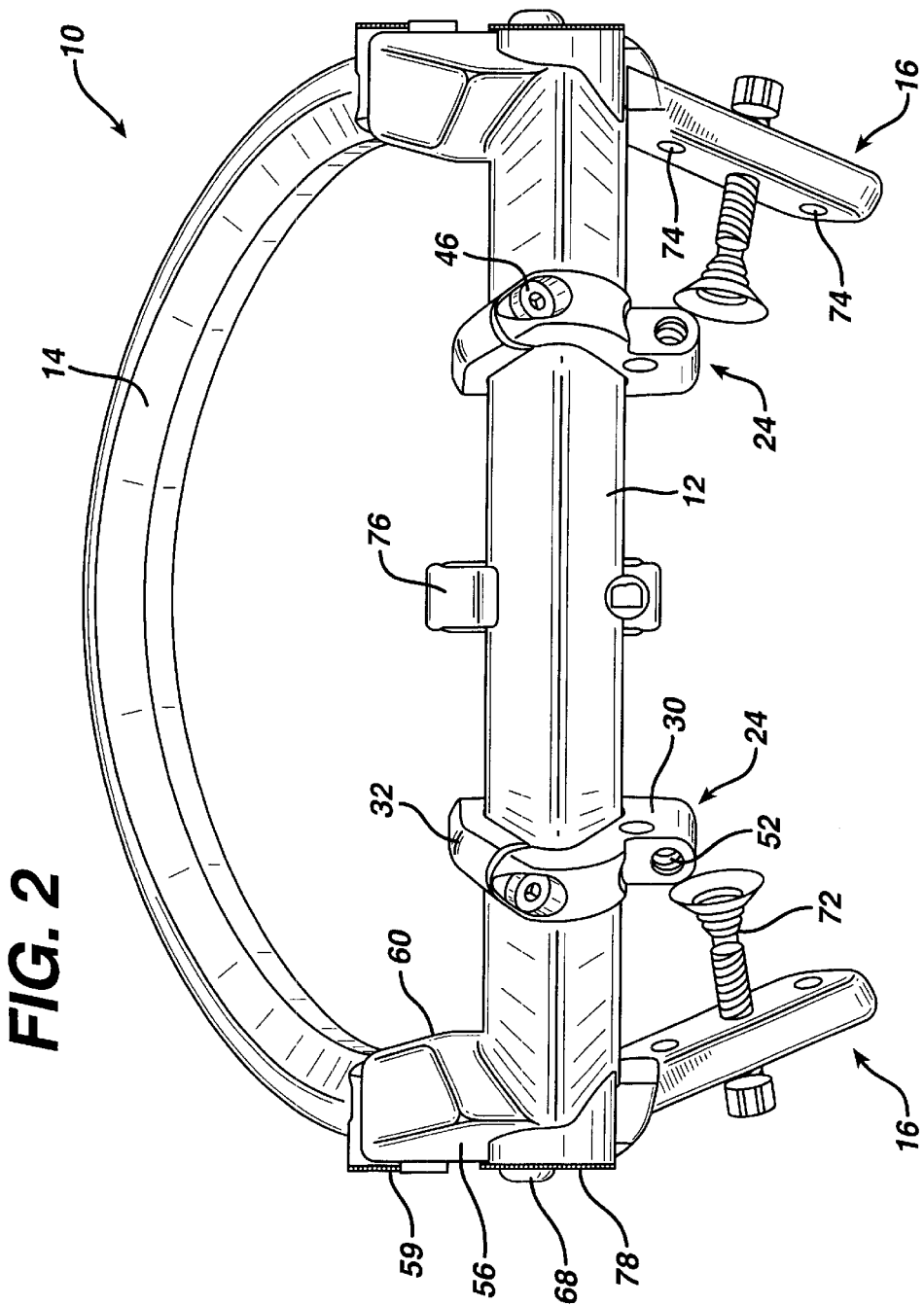
FIG. 2 is a front elevational view of the halo crown of FIG. 1.
Figure 3:
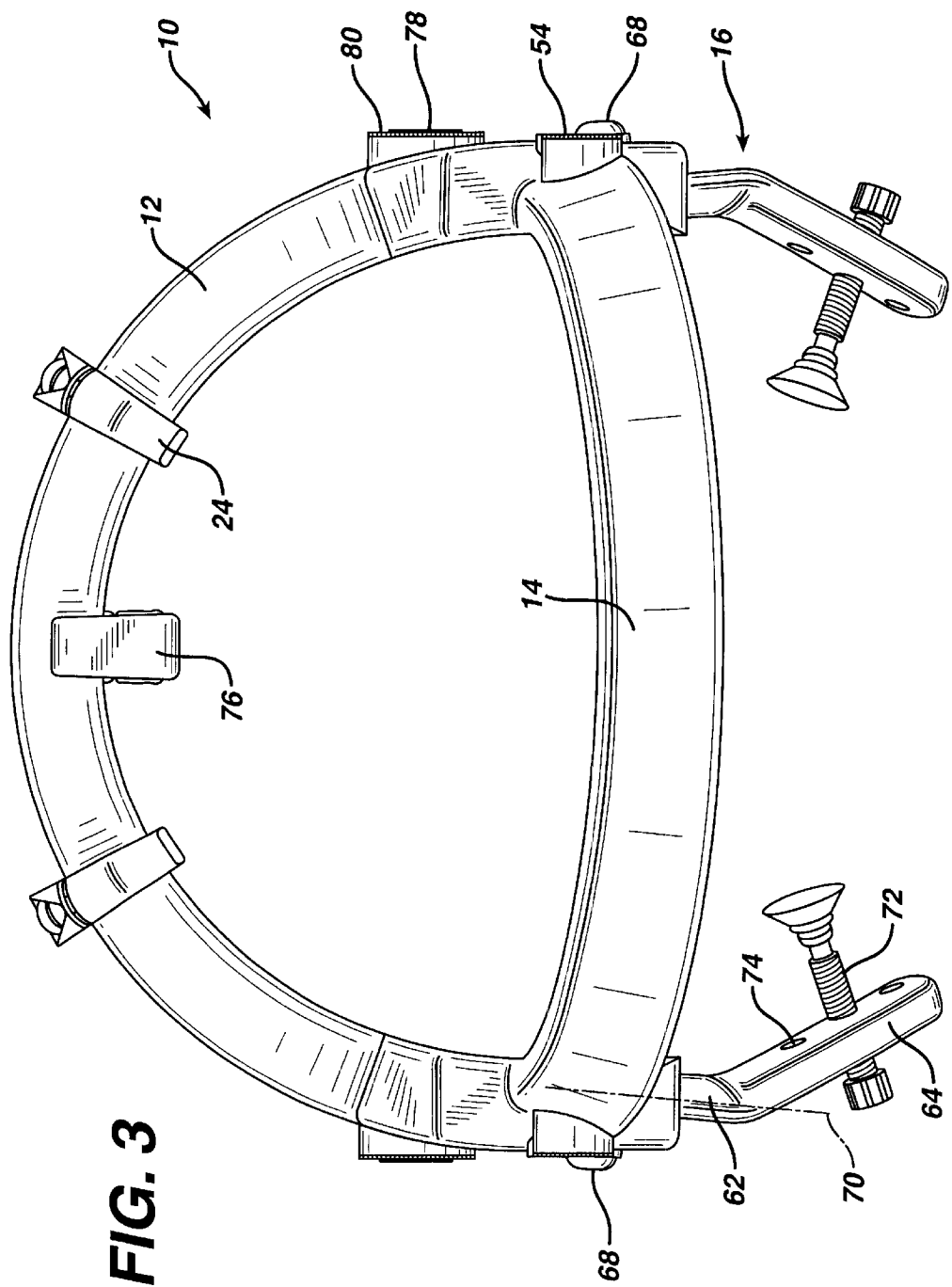
FIG. 3 is a top plane view of the halo crown of FIG. 1.

FIGS. 1–3 illustrate a halo crown 10 according to the present invention. It comprises generally an anterior arch 12 which encircles an anterior portion of a patient's skull (not shown) and a capital arch 14 which encircles a superior portion of the skull and connects to the anterior arch 12. A pair of adjustable legs 16 depend from first and second terminal ends, 18 and 20 respectively, of the anterior arch 12. Pins 22 (such as are commonly known in the art or a pin with a cutting tip as described by Voor in WO 98/30167) extend through the legs 16 and thru slideable members 24 along the anterior arch 12 to contact the patient's skull and affix the halo crown 10 in place.

Figure 4:
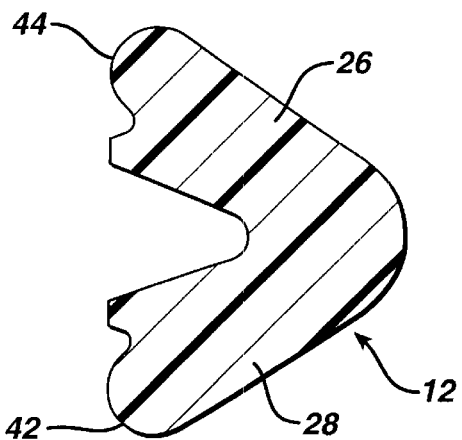
FIG. 4 is a cross-sectional view taken along lines 4—4 of FIG. 1.
Figure 5:
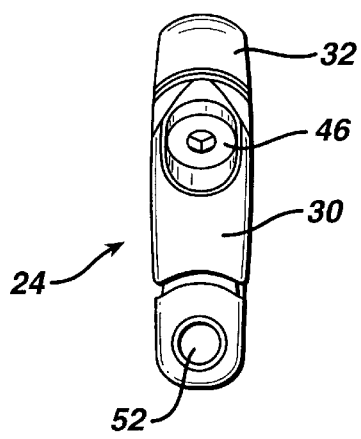
FIG. 5 is a detailed front elevation view of a slideable member of the halo crown of FIG. 1.
Figure 6:
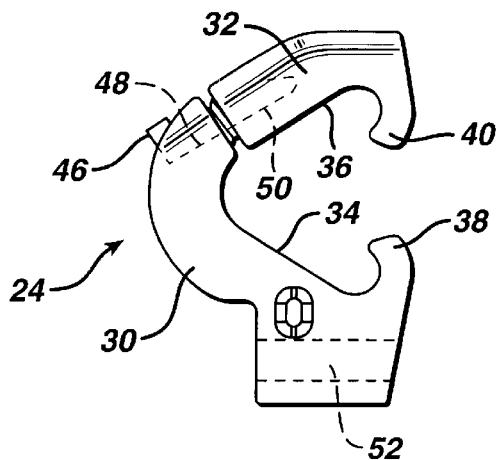
FIG. 6 is a side elevation view of the slideable member of FIG. 5.

The anterior arch 12 and capital arch 14 are preferably injection molded of a glass composite nylon 66 resin as an integral part. Such material is nonconductive and transparent to x-rays and MRI in a typical medical procedure. The anterior arch 12 has a v-shaped cross section (see also FIG. 4) having an upper v-portion 26 and lower v-portion 28. The slidable members 24 (see also FIGS. 5 and 6) have a complimentary internal triangular shape to receive and slide along the anterior arch 12. The slideable members 24 are preferably formed of aluminum but other materials may be substituted therefore.

Each slideable member 24 comprises a first half 30 and second half 32 with the first half 30 having an interior surface 34 conforming in shape to the lower v-portion 28 of the anterior arch 12 and the second half 32 having an interior portion 36 conforming in shape to the upper v-portion 26 of the anterior arch 12. Each of the interior surfaces 34 and 36 terminate in a hook 38 and 40 respectively to encircle terminal edges 42 and 44 of the lower v-portion 28 and upper v-portion 26 of the anterior arch 12, thereby affixing the slidable member 24 to the anterior arch 12 so that it can not be removed. A screw 46 extends through an aperture 48 through the first half 30 into a threaded aperture 50 in the second half 32. Tightening a screw 46 compresses the first and second halves 30 and 32 together and locks the slidable member 24 into a lateral position along the anterior arch 12. A threaded aperture 52 extends through the first half 30 to receive the pin 22.

The two-piece construction of the slideable member 24 allows it to be placed onto the halo crown 10 even after the halo crown 10 has been installed on a patient.

Figure 7:
FIG. 7 is a cross-sectional view taken along line 7—7 of FIG. 1.

Returning primarily to FIGS. 1–3, the capital arch 14 extends between the anterior arch 12 first and 18 and second end 20. Its cross-section is shown in FIG. 7. It provides rigidity to the halo crown 10. Threaded traction tong attachment holes 54 are provided on the capital arch 14 adjacent where it meets the anterior arch first end 18 and second end 20 and allow a pair of traction tongs to be affixed to the halo crown 10.

The legs 16 attach to receivers 56 integrally molded into and adjacent with the junction of the anterior arch 12 and capital arch 14. An open ended channel 58 is formed on an interior side 60 of each receiver 56. Each leg 16 comprises a first sliding portion 62 sized to be received within the channel 58 and a second depending portion 64 connected to the sliding portion 62. A slot 66 in the sliding portion 62 receives a bolt 68 which extends through the receiver 56 and locks the relative position of the sliding portion 62 to the receiver 56.

The leg depending portion 64 depends downwardly (inferiorly), inwardly (medially), and rearwardly (posteriorly) from the sliding portion 62. An axis 70 of the channel 58 extends slightly downwardly (inferiorly) and inwardly (medially). Thus, sliding the sliding portion 62 outwardly of the channel (posteriorly) causes the leg depending portion 64 to move rearwardly (posteriorly), outwardly (laterally) and downwardly (inferiorly). With one simple movement, the legs 16 can adjust to accommodate a large variety of skull sizes and shapes. Although shown as two straight sections the legs 16 can of course be curved or otherwise shaped to achieve the desired position. The shape of the legs 16 and orientation of the axis 70 simply and elegantly provide adjustment of the legs in three dimensions. Additional degrees of freedom can be provided beyond movement along the axis 70, such as rotational connections or sliding along additional axes to ,allow independent adjustment in three dimensions.

A positioning pad 72 threads through each leg depending portion 64 and one or more pin receiving apertures 74 extend therethrough as well. A c-shaped silicone pad 76 clips onto the anterior arch 12 between the slidable members 24.

The halo crown 10 is primarily meant to attach to a vest and rod assembly (not shown) as is known in art. Attachment apertures 78 are provided for this purpose. A ridged circular surface 80 surrounds the apertures 78 to allow rotational adjustment of the halo crown 10 with respect to the rod assembly.

To position the halo crown 10, the slidable members 24 are loosely attached to the anterior arch 12 such that they can slide along the inferior arch 12 but will not come off. The bolt 68 on the legs 16 is let loose so that the legs can also be moved. The halo crown 10 is positioned on the patient's skull with the pad 76 positioned at the forehead. The legs 16 are adjusted to provide good conformance between the legs and the patient's skull and the bolt 68 is tightened.

The positioning pads 72 are tightened against the skull thereby providing three points of contact to provisionally attach the halo crown 10 to the skull. The slideable members 24 are moved to an appropriate location along the anterior arch 12 and the screws 46 are tightened to lock the position of the slidable members 24 on the anterior arch 12. Four pins 22 are then driven into the patient's skull, one each through the pin apertures 52 in the slidable members 24 and one each through a pin aperture 74 on each leg 16. Of course more than four pins can be used. The positioning pads 72 and the c-shaped pad 76 can then be removed.

The present invention has been described above. Many modifications and variations thereof may be made without departing substantially from the spirit and scope of the present invention. Accordingly, it should be clearly understood that the form of the invention described and illustrated herein is exemplary only, and is not intended as a limitation on the scope.

What is claimed is:

1. A medical halo comprising:
   an elongated first arch shaped to generally extend about a portion of the periphery of an individual's head and to lie in laterally spaced relation thereto;
   at least one leg extending posteriorly from said first arch and extending over a posterior portion of the individual's head, said first arch comprises at least one channel formed therein having a first axis, and wherein at least a portion of the at least one leg is slidably disposed within the at least one channel, said leg being moveable along said first axis having a posterior-anterior component and a medial-lateral component; and
   at least one first contact member on said at least one leg.

2. A medical halo according to claim 1 wherein said first contact member is a pin clamp.

3. A medical halo according to claim 1 wherein said at least one leg comprises a first portion extending posteriorly from and slidably attached to said first arch and a second portion depending inferiorly from said first portion.

4. A medical halo according to claim 3 wherein said second portion also extends medially.

5. A medical halo according to claim 4 wherein said first portion also extends inferiorly and said first axis also has a posterior-inferior component.

6. A medical halo according to claim 5 wherein movement of the first portion along the first axis in one direction moves the second portion inferiorly, posteriorly and laterally, and movement of the first portion along the first axis in an opposite direction moves the second portion superiorly, anteriorly and medially.

7. A medical halo according to claim 1 further comprising a positioning pad on said first arch.

8. A medical halo according to claim 7 wherein said positioning pad is elastomeric and shaped to elastically fit onto the first arch.

9. A medical halo according to claim 1 further comprising a second arch connected to the first arch and out of planar relationship with the first arch whereby to provide rigidity to the first arch.

10. A medical halo according to claim 1 wherein the first arch is injection molded.

11. A medical halo according to claim 1 having two legs.

12. A medical halo according to claim 1 and further comprising at least one slideable member slideably affixed to the first arch and bearing a second contact member.

13. A medical halo according to claim 12 wherein the first arch and the at least one slideable member have complimentary interlocking shapes such that the slideable member is slideable along the first arch yet can not rotate around the first arch.

14. A medical halo according to claim 12 wherein the at least one slideable member can be affixed to the first arch after the medical halo has been installed on the individual's head.

15. A medical halo according to claim 14 wherein the at least one slideable member comprises a first section and a second section which are separable from one another whereas to allow the slideable member to be affixed to the first arch after the medical halo has been installed on the individual's head.

* * * * *

UNITED STATES PATENT AND TRADEMARK OFFICE
CERTIFICATE OF CORRECTION

PATENT NO.    : 6,468,238 B1
DATED         : October 22, 2002
INVENTOR(S)   : J. Riley Hawkins, John Knapik and Eric Smith It is certified that error appears in the above-identified patent and that said Letters Patent is hereby corrected as shown below:

<u>Column 3,</u>
Line 39, please delete "inferior" and replace with -- anterior --.

Signed and Sealed this

Second Day of September, 2003

JAMES E. ROGAN
*Director of the United States Patent and Trademark Office*